US008886792B2

(12) United States Patent
Biondi et al.

(10) Patent No.: US 8,886,792 B2
(45) Date of Patent: Nov. 11, 2014

(54) METHOD AND APPARATUS FOR DISPLAYING AND STORING DATA FROM MEDICAL DEVICES AND ALARMING IN RESPONSE TO TRIGGERS BY A PLURALITY OF ALARM TYPES

(75) Inventors: James W. Biondi, North Haven, CT (US); Joseph P. McGuire, Orange, CT (US); Carter Thomas Comunale, Southbury, CT (US)

(73) Assignee: Cardiopulmonary Corp., Milford, CT (US)

( * ) Notice: Subject to any disclaimer, the term of this patent is extended or adjusted under 35 U.S.C. 154(b) by 292 days.

(21) Appl. No.: 12/902,536

(22) Filed: Oct. 12, 2010

(65) Prior Publication Data

US 2011/0087756 A1      Apr. 14, 2011

Related U.S. Application Data

(60) Provisional application No. 61/250,947, filed on Oct. 13, 2009.

(51) Int. Cl.
*G06F 15/173*      (2006.01)
*G06F 19/00*       (2011.01)
*H04L 12/24*       (2006.01)

(52) U.S. Cl.
CPC ........ *G06F 19/3418* (2013.01); *H04L 12/2419* (2013.01)
USPC ....................................................... 709/224

(58) Field of Classification Search
CPC ................................................. H04L 12/2419
USPC .................. 709/204, 205, 217, 224; 715/772; 707/704
See application file for complete search history.

(56) References Cited

U.S. PATENT DOCUMENTS 4,163,218 A      7/1979   Wu
4,206,456 A *    6/1980   Malinowski et al. ......... 340/630

(Continued)

FOREIGN PATENT DOCUMENTS

JP      2007086872      4/2007
WO      9829790         7/1998

(Continued)

OTHER PUBLICATIONS

PAX, United States Statutory Invention Registration No. H727, "Patient Monitoring Device," published Jan. 2, 1990.

(Continued)

*Primary Examiner* — Lance L Barry
(74) *Attorney, Agent, or Firm* — K&L Gates LLP

(57) ABSTRACT

The invention, in one aspect, relates to a system for providing for the display of data from a plurality of non-homogeneous medical devices. In one embodiment the system includes a local authority to receive data using a first protocol from the medical devices and convert the data to a second protocol, a central authority in communication with the local authority, and a user interface, in communication with the central authority. The central authority routes data that has been converted to a second protocol for display by the user interface. The system generates alarms when a data value from one medical device reaches an alarm limit; deviates from a setting as a deviation alarm; and when a combination of data values from more than one medical device occurs, as a combination alarm; and if an alarm is triggered more than a predetermined number of times, as a consecutive alarm.

13 Claims, 11 Drawing Sheets

(56) References Cited

U.S. PATENT DOCUMENTS

| | | |
|---|---|---|
| 4,333,002 A | 6/1982 | Kozak |
| 4,371,932 A | 2/1983 | Dinwiddie, Jr. et al. |
| 4,417,573 A | 11/1983 | De Vries |
| 4,530,696 A * | 7/1985 | Bisera et al. ............... 604/253 |
| 4,869,266 A * | 9/1989 | Taylor et al. ............... 600/587 |
| 4,915,450 A | 4/1990 | Cooper |
| 4,958,645 A | 9/1990 | Cadell et al. |
| 4,972,314 A | 11/1990 | Getzinger et al. |
| 5,002,060 A | 3/1991 | Nedivi |
| 5,003,984 A | 4/1991 | Muraki et al. |
| 5,023,823 A | 6/1991 | Cargin, Jr. et al. |
| 5,049,873 A | 9/1991 | Robins et al. |
| 5,056,864 A | 10/1991 | Cooper |
| 5,238,001 A | 8/1993 | Gallant et al. |
| 5,319,355 A | 6/1994 | Russek |
| 5,319,363 A | 6/1994 | Welch et al. |
| 5,379,250 A | 1/1995 | Harshfield |
| 5,386,532 A | 1/1995 | Sodos |
| 5,441,047 A | 8/1995 | David et al. |
| 5,452,356 A | 9/1995 | Albert |
| 5,481,255 A | 1/1996 | Albert et al. |
| 5,482,050 A | 1/1996 | Smokoff et al. |
| 5,491,796 A | 2/1996 | Wanderer et al. |
| 5,511,553 A | 4/1996 | Segalowitz |
| 5,673,692 A | 10/1997 | Schulze et al. |
| 5,685,314 A | 11/1997 | Geheb et al. |
| 5,687,717 A | 11/1997 | Halpern et al. |
| 5,923,557 A | 7/1999 | Eidson |
| 5,944,659 A | 8/1999 | Flach et al. |
| 5,960,403 A | 9/1999 | Brown |
| 5,974,463 A | 10/1999 | Warrier et al. |
| 5,987,519 A | 11/1999 | Peifer et al. |
| 6,074,345 A | 6/2000 | van Oostrom et al. |
| 6,104,333 A | 8/2000 | Wood, Jr. |
| 6,112,194 A | 8/2000 | Bigus |
| 6,122,639 A | 9/2000 | Babu et al. |
| 6,128,371 A | 10/2000 | Hazama |
| 6,151,308 A | 11/2000 | Ibanez-Meier et al. |
| 6,158,430 A | 12/2000 | Pfeiffer et al. |
| 6,213,954 B1 | 4/2001 | Chen |
| 6,304,788 B1 | 10/2001 | Eady et al. |
| 6,339,771 B1 | 1/2002 | Zimowski et al. |
| 6,402,691 B1 | 6/2002 | Peddicord et al. |
| 6,408,330 B1 | 6/2002 | DeLaHuerga |
| 6,556,321 B1 | 4/2003 | Milton et al. |
| 6,589,170 B1 | 7/2003 | Flach et al. |
| 6,602,191 B2 | 8/2003 | Quy |
| 6,612,984 B1 | 9/2003 | Kerr, II |
| 6,618,709 B1 | 9/2003 | Sneeringer |
| 6,640,246 B1 | 10/2003 | Gary, Jr. et al. |
| 6,690,274 B1 * | 2/2004 | Bristol ............... 340/506 |
| 6,693,545 B2 * | 2/2004 | Brown et al. ............... 340/573.1 |
| 6,757,898 B1 | 6/2004 | Ilsen et al. |
| 6,832,199 B1 | 12/2004 | Kucek et al. |
| 6,839,753 B2 | 1/2005 | Biondi et al. |
| 6,942,616 B2 | 9/2005 | Kerr, II |
| 6,968,375 B1 | 11/2005 | Brown |
| 6,988,088 B1 | 1/2006 | Miikkulainen et al. |
| 6,989,757 B2 * | 1/2006 | Geoffrey et al. ............... 340/632 |
| 7,088,233 B2 | 8/2006 | Menard |
| 7,221,137 B2 * | 5/2007 | Bae et al. ............... 324/72 |
| 7,415,297 B2 * | 8/2008 | Al-Ali et al. ............... 600/323 |
| 7,936,259 B1 * | 5/2011 | Weibel et al. ............... 340/506 |
| 8,126,505 B2 * | 2/2012 | Tulloch ............... 455/557 |
| 8,515,513 B2 * | 8/2013 | Batchelder et al. ............ 600/324 |
| 2001/0051787 A1 | 12/2001 | Haller et al. |
| 2003/0023146 A1 | 1/2003 | Shusterman |
| 2003/0177036 A1 | 9/2003 | Oka et al. |
| 2005/0114711 A1 | 5/2005 | Hesselink et al. |
| 2005/0146431 A1 | 7/2005 | Hastings et al. |
| 2005/0188083 A1 * | 8/2005 | Biondi et al. ............... 709/224 |
| 2005/0206518 A1 | 9/2005 | Welch et al. |
| 2008/0004904 A1 | 1/2008 | Tran |
| 2008/0065768 A1 | 3/2008 | Ortiz et al. |
| 2008/0300471 A1 * | 12/2008 | Al-Ali et al. ............... 600/301 |
| 2009/0045937 A1 * | 2/2009 | Zimmerman ............... 340/506 |
| 2009/0125178 A1 * | 5/2009 | Wilson ............... 701/33 |
| 2010/0078030 A1 * | 4/2010 | Colburn ............... 128/207.14 |
| 2012/0095304 A1 * | 4/2012 | Biondi ............... 600/301 |

FOREIGN PATENT DOCUMENTS

| | | |
|---|---|---|
| WO | 0040145 | 7/2000 |
| WO | 0060522 | 10/2000 |
| WO | 0113190 | 2/2001 |
| WO | 03043494 | 5/2003 |

OTHER PUBLICATIONS

Brunner, et al., "Prototype Ventilator and Alarm Algorithm for the NASA Space Station," Journal of Clinical Monitoring, 5(2):90-99 (1989).

Shabot, "Standardized acquisition of bedside data: The IEEE P1073 medical information bus," International Journal of Clinical Monitoring and Computing, 6:197-204 (1989).

Silvern et al., "Ventilator Risk Management Using a Programmed Monitor," Journal of Clinical Engineering, 14 (3):217-224 (May/Jun. 1989).

PCT International Search Report and Written Opinion of International Searching Authority for International Patent Application No. PCT/US2010/052271, mailed Mar. 24, 2011, 12 pages.

Japanese Official Action for Japanese Patent Application No. 2012-534279, 3 pages, Jul. 16, 2014.

Machine Translation of Japanese Publication No. 2007-086872, Published on Apr. 5, 2007.

* cited by examiner

| Monitor | 80 | | | | |
|---|---|---|---|---|---|
| Bed 3012: J. Smith  Low SPO2 Alarm | | Bed 3014: T. Hopkins | | Bed 3016: E. Russell | |
| SPO2  78% | SPO2 Pulse Rate  58 bpm | SPO2  95% | SPO2 Pulse Rate  66 bpm | ETCO2  21 | ETCO2RR  23 bpm  FICO2  0 |
| Bed 3013: R Reynolds | | Bed 3015: K Linder | | Bed 3017: P. Fillipo | |
| SPO2  91% | SPO2 Pulse Rate  70 bpm | SPO2  99% | SPO2 Pulse Rate  62bpm | Pulse Oximeter Monitoring Suspended | |
| | | ETCO2  35 | ETCO2RR  19 bpm  FICO2  0 | | |
| 3/31/2009  12:22:33 PM | | | Monitor | Report | Administer Unassigned |

FIG. 2

ALARM SET UP

M5208 | R STREEPY

LIMIT ALARMS

| Alarm Name | High Limit | Low Limit | Units |
|---|---|---|---|
| ART 1 (DIA) Limit | 120 | 20 | mmHg |
| ART 1 (MAP) Limit | 180 | 60 | mmHg |
| ART 1 (SYS) Limit | 143 | 90 | mmHg |
| ART2 (DIA) Limit | 120 | 20 | mmHg |
| ART2 (MAP)Limit | 180 | 60 | mmHg |
| ART2 (SYS) Limit | 150 | 85 | mmHg |
| HR Limit | 140 | 45 | bpm |
| INVP1 (DIA) Limit | 120 | 20 | mmHg |
| INVP1 (MAP) Limit | 180 | 60 | mmHg |
| INVP1 BP (SYS) Limit | 150 | 90 | mmHg |
| NBP (DIA) Limit | 120 | 20 | mmHg |
| NBP (MAP) Limit | 180 | 60 | mmHg |

CONSECUTIVE ALARMS

| Alarm Name | Limit | No. of Occurrences | Time Period (min) |
|---|---|---|---|
| JCP | 20 | 3 | 3 |
| Bradycardia | 50 | 3 | 3 |
| Tachycardia | 130 | 3 | 3 |

Valid range: 240-40. Defaults (high: 150, low: 90)

Restore Defaults | APPLY | CANCEL | OK

- A4E1
- A4E2
- A5E1
- A5E2
- ACC1
- ACC2
- ACC3
- CV2A
- CV2B
- CV3A
- MICU1
- MICU2
- MPCU
- NCC1
  - M5201 | T Cessie
  - M5205 | M CTPK
  - M5206 | B BLACKFORD
  - M5208 | R STREEPY
  - M5209 | A HONEYCUTT
  - M5210 | G CTSMITH
  - M5222 | B DOBBS
  - M5223 | J JONES
- NCC2
- NORTH
- NSICU

FIG. 3

| | | | |
|---|---|---|---|
| M4329 \| B JONES | VENT FIB/TACH<br>⊙ 2/25/2009 9:28:19 PM | 73<br>HR/min | Time:<br>14:08:58 |
| M4322 \| P TTESTNPSG | VENT FIB/TACH<br>⊙ 2/25/2009 4:30:18 PM | 96<br>HR/min | Time:<br>19:06:47 |
| M4321 \| | SPO2 Limit 85<86<br>⊙ 3/2/2009 11:48:23 AM | 91<br>%SPO2 | Time:<br>00:01:20 |
| M4325 \| | HR Limit 142>140<br>⊙ 3/2/2009 11:47:23 AM | 137<br>HR/min | Time:<br>00:02:20 |
| M4326 \| c oakes | NBP (SYS) Limit 83/45 (53)<90<br>⊙ 3/2/2009 11:46:23 AM | 83/45 (53)<br>NBP | Time:<br>00:01:24 |
| M4326 \| c oakes | NBP (MAP) Limit 83/45 (53)<60<br>⊙ 3/2/2009 11:46:23 AM | 83/45 (53)<br>NBP | Time:<br>00:01:24 |
| M4305 \| R O'LEARY O'GRADY | ART2 (MAP) Limit 118/44 (57)<60<br>⊙ 3/2/2009 11:41:23 AM | 118/44 (57)<br>ART2 | Time:<br>00:09:25 |
| M4306 \| R O'LEARY O'GRADY | NBP (SYS) Limit 158/111 (123)>150<br>⊙ 3/2/2009 11:41:24 AM | 158/111 (123)<br>NBP | Time:<br>00:01:31 |
| M4306 \| R O'LEARY O'GRADY | NBP (DIA) Limit 177/128 (140)>120<br>⊙ 3/2/2009 11:32:23 AM | 158/111 (123)<br>NBP | Time:<br>00:04:25 |
| M4302 \| O CTPHYSATTENDREL | RR Limit 44>40<br>⊙ 3/2/2009 2:45:22 AM | 17<br>RESP | Time:<br>08:51:23 |
| M4317 \| B TYSON | HR Limit 142>140<br>⊙ 3/2/2009 1:03:22 AM | 84<br>HR/min | Time:<br>10:33:37 |
| M4301 \| g onstott | ART2 (MAP) Limit 91/45(59)<60<br>⊙ 3/2/2009 12:07:22 AM | 99/47(64)<br>ART 2 | Time:<br>11:29:23 |
| M4301 \| g onstott | ART2 (SYS) Limit 86/39(53)<90<br>⊙ 3/1/2009 10:48:22 PM | 99/47(64)<br>ART 2 | Time:<br>12:48:23 |
| M4320 \| T CTPHYSATTENDREL | HR Limit 152>140<br>⊙ 3/1/2009 10:04:22 PM | 95<br>HR/min | Time:<br>13:32:41 |
| M4311 \| P TTESTNPSG | RR Limit 0<6<br>⊙ 3/1/2009 7:13:22 PM | 30<br>RESP | Time:<br>16:23:33 |
| M4329 \| B JONES | NBP (DIA) Limit 150/121/(125)>120<br>⊙ 3/1/2009 7:01:22 PM | 105/56(67)<br>NBP | Time:<br>16:35:57 |

Nurse Call  ☒

» Room: -
Patient: -
3/2/2009 11:48:06 AM
10.8.237.60

Current: 3/2/2009 11:50:49 AM
Last: 3/2/2009 11:50:50 AM

Selected Units
A4E1, A4E2

FIG. 4

| Administration |
|---|
| Admit New Patient |
| Add Medical Device |
| D/C Medical Device |
| Swap Medical Device |
| Edit Patient Data |
| Transfer Patient |
| Pager Assignment |
| Smart Alarms |
| Workstation View |

| Bed | Patient | Device | Primary Alert | Secondary Alert |
|---|---|---|---|---|
| 3012 | Smith, J., 922918177 | 12489509-126952 (Alaris) | | ☐ |
| 3013 | Reynolds, R., 9234181117 | 12489637-126978 (Alaris) | | ☐ |
| 3014 | Hopkins, T., 9299191818 | 12489509-126982 (Alaris) | | ☐ |
| 3015 | Linder, K., 99199102893 | 12489637-126978 (Alaris) | | ☐ |
| 3016 | Russell, E., 94329100012 | 12489509-126982 (Alaris) | | ☐ |
| 3017 | Filippo, P., 910929910190 | 12489637-126978 (Alaris) | | ☐ |

| Unassigned |
|---|
| PCU (32) |
| PCA (3) |
| LVP (56) |

Updated 12:23:18 PM

Print
Version
Rev M (BUILD-10141) Decn320

3/31/2009
12:23:24 PM

| | Monitor | Report | Administer Unassigned |

| Begin | Back |

Log of Events
Patient: 2512
Filter: 'Alarms', 'Setting Changes', 'Events', 'ADT', 'Admin', 'Smart Alarms'.
Date: 3/2/2009 7:57:56 AM to 3/2/2009 11:57:56 AM
Page 2, descending order

| Time | Event |
|---|---|
| Monday, March 02, 2009 | |
| 11:40:14 AM | Connection Lost to the Local Authority: 10.16.10.70 |
| 11:38:30 AM | VTACH alarm reset by user: bernoulli |
| 11:38:27 AM | ASYSTOLE alarm reset by user: bernoulli |
| 11:38:24 AM | VTACH alarm reset by user: bernoulli |
| 11:38:17 AM | VTACH alarm reset by user: bernoulli |
| 11:37:54 AM | VENT FIB/TACH alarm reset by user: bernoulli |
| 11:37:50 AM | VENT FIB/TACH alarm reset by user: bernoulli |
| 11:37:40 AM | VTACH alarm reset by user: bernoulli |
| 11:37:17 AM | VTACH alarm reset by user: bernoulli |
| 11:37:17 AM | ASYSTOLE alarm reset by user: bernoulli |
| 11:37:12 AM | VTACH alarm reset by user: bernoulli |
| 11:37:00 AM | VTACH alarm reset by user: bernoulli |
| 11:34:12 AM | bernoulli logged in |
| 11:15:19 AM | bernoulli logged in |
| 10:30:22 AM | Connection reestablished data feed: 10.0.114.33 : 10.16.10.70 |
| 10:29:53 AM | Connection lost to data feed: 10.0.114.33 : 10.16.10.70 |
| 9:09:23 AM | |
| 8:10:22 AM | Connection reestablished to data feed: 10.0.114.33 : 10.16.10.70 |
| 8:09:53 AM | Connection lost to data feed: 10.0.114.33 : 10.16.10.70 |

Print

Prev

| REPORTS | ADMIN | NURSE LOG | PHYSICIAN LOG | Monday, March 02, 2009 11:58:23 AM | LOGOUT |

METHOD AND APPARATUS FOR DISPLAYING AND STORING DATA FROM MEDICAL DEVICES AND ALARMING IN RESPONSE TO TRIGGERS BY A PLURALITY OF ALARM TYPES

CROSS-REFERENCE TO RELATED APPLICATIONS

This application claims priority to U.S. Provisional Patent Application 61/250,947 filed on Oct. 13, 2009, the disclosure of which is herein incorporated by reference in its entirety.

FIELD OF THE INVENTION

The invention relates generally to the field of medical devices and more specifically to the field of transforming and displaying patient data from medical devices in a central location.

SUMMARY OF THE INVENTION

The invention, in one aspect, relates to a system for providing for the display of data from a plurality of non-homogeneous medical devices. In one embodiment the system includes a local authority to receive data using a first protocol from the medical devices and convert the data to a second protocol, a central authority in communication with the local authority, and a user interface, in communication with the central authority. The central authority routes data that has been converted to a second protocol for display by the user interface.

In another embodiment, the first protocol is a native device protocol and the second protocol is a homogeneous system protocol. In one embodiment, the homogenous system protocol is XML. In yet another embodiment, the first protocol is a Transmission Control Protocol/Internet Protocol (TCP/IP) and the second protocol is a combination of TCP with another protocol referenced herein as XML, CPC XML or TCP/CPC XML.

In another embodiment the system further includes a smart alarm module in communication between the local authority and the central authority. The smart alarm module determines whether the data from the medical device meets a predetermined criterion for triggering an alarm. In yet another embodiment the system further includes a database in communication with the smart alarm module. In still yet another embodiment the system further includes a database interface in communication with the central authority and a database.

In one embodiment the system further includes an internet information server in communication between a database and a web interface. In another embodiment the system further includes a configuration service in communication with a database, a smart alarm module and the user interface. In yet another embodiment the system further includes a de-multiplexer in communication between the local authority and the medical devices. In still yet another embodiment the local authority is located physically near to the central authority, while in another embodiment the local authority is located physically near to the medical devices.

Another aspect of the invention is a method for providing for the display of data from a plurality of non-homogeneous medical devices. In one embodiment the method includes the steps of: receiving data using a first protocol from the medical devices by a local authority, converting the data to a second protocol by the local authority, transmitting the data in the second protocol by the local authority to a central authority, transmitting the data in the second protocol by the central authority to a user interface; and displaying the data by the user interface.

In another embodiment, the method further includes the step of determining, by a smart alarm module, whether the data from the medical device meets a predetermined criterion for triggering an alarm. In yet another embodiment the method further includes demultiplexing data from the medical devices prior to converting the data to the second protocol by the local authority.

This application incorporates the disclosures of U.S. patent application Ser. No. 10/984,186 filed on Nov. 8, 2004 and U.S. Pat. No. 6,839,753 filed on Feb. 23, 2001 in their entirety.

BRIEF DESCRIPTION OF THE DRAWINGS

The invention is pointed out with particularity in the appended claims. The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

FIG. 2 shows an embodiment of a view of various patient icons with supplemental information of interest;

FIG. 3 shows an embodiment of another user interface screen that is accessed to set the smart alarms;

FIG. 4 shows an embodiment of an overview screen listing the smart alarms which are set for each patient;

FIG. 5 is a screenshot of an embodiment of a graphic user interface suitable for performing various administrative functions relative to the medical device monitoring system of the invention;

FIG. 7 is a screen shot for another monitoring screen;

FIG. 8 depicts an embodiment of a log screen; and

FIG. 9 depicts an embodiment of a user interface for showing various patient trends over time.

Reference to CPC XML or TCP/CPC XML in the figures and application encompasses the broader usage of XML as well as XML that contains information relating to medical devices and medical device data. Thus, in one embodiment, CPC XML refers to XML or XML that transmits or includes medical device or patient information or is otherwise modified to work with a patient monitoring system. Similarly, in one embodiment, TCP/CPC XML, refers to TCP or XML, as well as TCP and XML that transmits or includes medical device or patient information or are otherwise modified to work with a patient monitoring system.

DESCRIPTION OF THE PREFERRED EMBODIMENT

Figure 1:
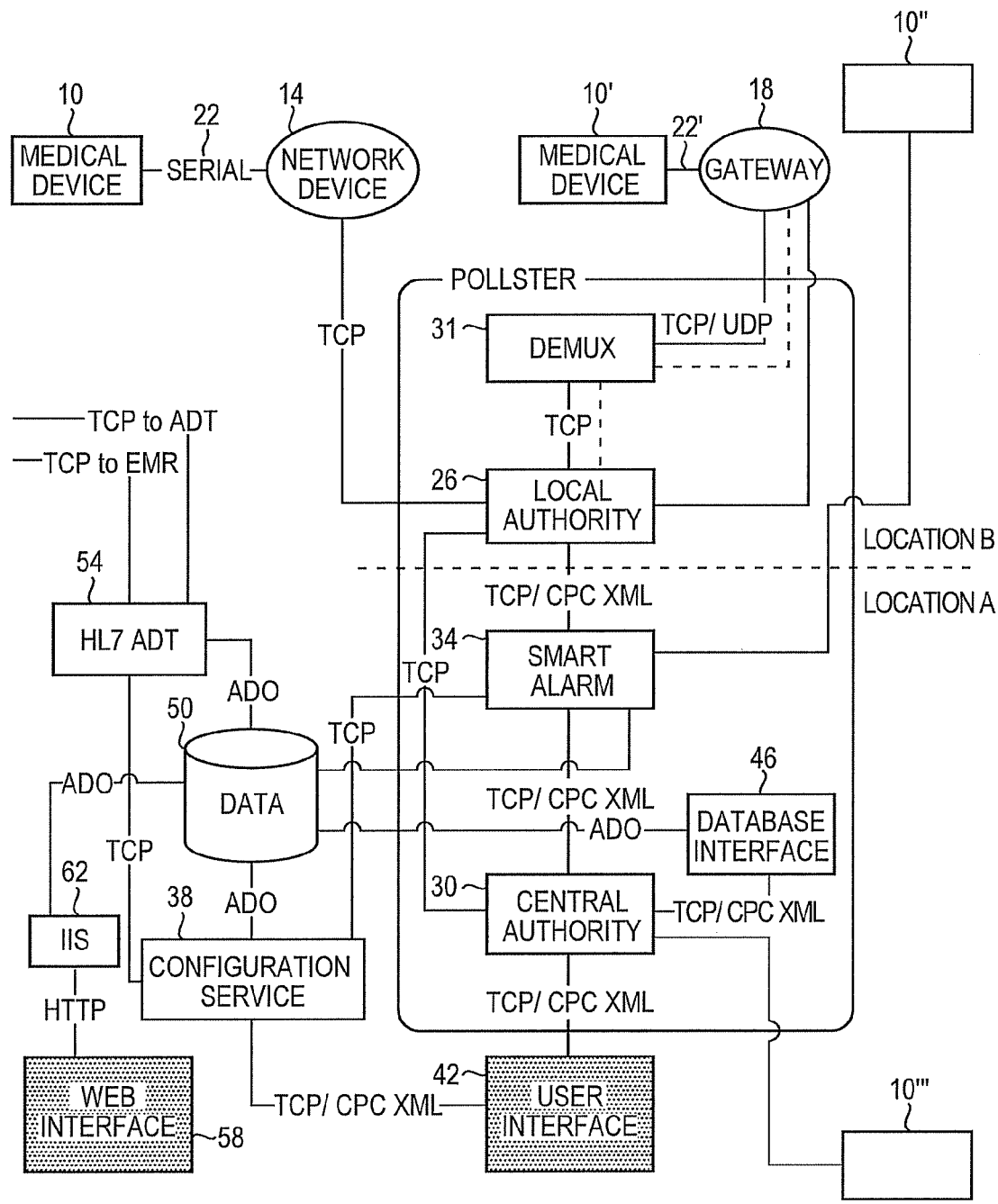
FIG. 1 is a block diagram of an embodiment of the system of the invention.

In brief overview and referring to FIG. 1, in one embodiment, heterogeneous medical devices 10, 10', 10'', 10''' (generally 10) are connected to the system of the invention in multiple ways. The medical devices 10 typically have a serial output 22, 22', respectively, for device specific data such as patient data. In general, the medical devices and the system monitor patients to collect patient data which is transformed and processed such that improved medical treatment and patient safety results. Various types of medical devices with their own native devices protocols can be used in one embodiment. Further, in one embodiment, as used herein, the term medical device can include, but is not limited to any device used to collect patient data, assist with patient safety or otherwise be used to facilitate medical treatment or diagnosis of one or more patients. In one embodiment, the medical device's native protocol is translated, transformed or remapped into a homogeneous protocol that is used by the system to communicate with or otherwise exchange data with the various heterogeneous medical devices 10.

In another embodiment, a medical device 10''' connects to the system through the central authority 30 (discussed below). Alternatively, the medical device 10' can also connect to the local authority using the gateway 18. In still another embodiment, a medical device 10'' connects to the system through a smart alarm module 34 (discussed below).

In one embodiment shown, the serial output port 22 of the medical device 10 is connected to a network device 14 which changes the serial output of the medical device 10 to a protocol suitable for use over the network such as the internet transmission control protocol (TCP/IP). In another embodiment, the serial output port 22' of medical device 10' is connected to a gateway 18. The gateway 18 permits several medical devices 10' to be connected to the gateway 18 and forms a data connection by multiplexing the data from each of the devices 10' into a single data stream suitable for transmission over a network using the TCP/IP or user datagram protocol (UDP).

In a third embodiment, the medical device is 10'' is connected to the system through a smart alarm 34. In another embodiment, the medical device 10''' is connected to the system through the central authority 30.

In the embodiment in which the medical device 10 is connected to a network device 14, when the data arrives from a network device, the TCP/IP packet is received directly by a local authority 26. In the second embodiment, if the data arrives from a gateway 18, the data is passed through a de-multiplexer 30 prior to being sent to the local authority 26. The demultiplexer 31 or demux separates the TCP/IP or UDP packet into a separate TCP/IP packet for each device 10'. In one embodiment, an alternative communication channel 19 is present such that the gateway 18 and the local authority 26 exchange data without the demultiplexer 31.

Depending on the embodiment, the local authority 26 either then sends the data to the central authority 30 or the smart alarm module 34. If the data is sent from the local authority 26 to the central authority 30 directly, the communication in one embodiment utilizes the TCP/IP protocol. If the data is sent by the local authority 26 to the smart alarm module 34, the messages are sent using a homogenous system protocol such as TCP/IP, XML, the TCP/CPC XML protocol, or another suitable protocol. In one embodiment, the CPC XML protocol is used because it provides various advantages.

One advantageous reason for the use of an XML based protocol in combination with a traditional TCP protocol is that in one embodiment the medical device monitoring system uses TCP/IP sockets to transmit certain medical device data. This medical device data describes the state of medical devices connected to the monitoring system. In contrast, in one exemplary implementation, XML documents are generated by client bridges (serial to Ethernet converters), system wide servers, or directly from the medical devices themselves. Any component or device (medical device, server, bridge, etc.) that generates and transmits data is determined by the system to be publisher. Since TCP/IP sockets are used in combination with XML documents, a two protocol system is used to manage data routed to the overall monitoring system. Additional detail and description relating to publishers is provided below in the discussion of FIG. 10B.

When a component or device is treated as publisher with the associated responsibility of gathering data from one or more medical devices, such a publisher is known as a Local Authority 26. Local Authorities provide device data to a system responsible for distributing information to interested data subscribers as shown in FIG. 10B.

In one embodiment the local authority 26 is located physically in the same location as the central authority 30. In other embodiments, the local authority 26 and any de-multiplexer 30 are located physically near the medical device 10' or may be part of the gateway 18 itself. In general, the topologies shown in the figures and various modules, interfaces, subsystems, systems, etc. can be combined or separated by function or location as appropriate for a given patient monitoring scenario. In one embodiment, different elements of the system can be located at different locations. For example, as shown in FIG. 1, in some embodiments, different elements of the system, can be separated and located at different physical locations. In one embodiment, the system is separated into components at different physical locations A and B as shown.

The smart alarm module 34 is used to generate additional alarms when the data from the medical device 10, 10', deviates from values set by the clinician. In this manner the clinician may set alarms, for example based on the rate of change of a parameter, which are not available directly from the medical devices 10, 10' themselves. For example, alarms generated by the smart alarm module 34 are sent to the central authority 30 using the homogenous system protocol. Values defining the smart alarm set values are written to the smart alarm module 34 by a configuration service 38 using the TCP/IP protocol, another protocol, or the homogenous system protocol.

The data received by the central authority 30 either from the local authority 26 or the smart alarm 34 is transmitted to the User Interface 42 using the homogenous system protocol. The central authority 30 also transmits the a message based on the homogenous system protocol such as a TCP/CPC XML message to a database interface 46. The database interface 46 converts the homogenous data to an activeX data object (ADO) for storage in a database 50. In this way events received by the system can be logged, including the smart alarms.

The user interface 42 writes data to the configuration server 38 using a homogenous system protocol such as the TCP/CPC XML protocol. In turn the data is written to the database 50 by the configuration server using the ADO. The database 50 is also written to by the administrative tool HL7ADT which in turn is written to by the configuration server 38 using TCP. The administrative tool is used to update the patient information. The administrative tool HL7ADT also receives information from and transmits data to patient electronic medical records (EMR) and patient admission, discharge, and transfer records (ADT) at, for example, a hospital or other heath care provider (or a subunit thereof).

Finally, the web interface 58 permits browser access to the system. In one embodiment, access is granted using the HTTP secure protocol. The Web interface 58 uses the internet information services 62 to read and write data to the database 50 using ADO.

Considering each of the modules individually, the smart alarm module 34 reviews the data as it is received from the local authority 26. The data associated with the patient is compared to alarm settings for various parameters as stored in the database. When an alarm is triggered the alarm is displayed on multiple user screens through the user interface 42.

In some embodiments, bypassing the database provides various speed and data processing advantages. By splitting the data stream and replicating it, the system scales. As a result, the system can offload work to other devices (servers, processors, routers, hubs, etc.). For example, when an XML packet comes in, the system can duplicate it, redirect it, and send it out over two different streams or channels. This splits any processing or delivery load associated with those two split streams. As part of the routing and data delivery described herein, each data stream can be continuously duplicated and split repeatedly to further distribute processing and transport load. In one embodiment, the cost associated with doing so is the time used to split the data streams. This time period is typically controlled to be a sufficiently small period of time relative to instrument sensitivity and timing needs associated with maintaining patient safety.

One example of a homogenous system protocol is XML. XML has well developed standard developer tools. In addition, XML has advantages. For example, a flexible data packet can be generated that can handle inputs from various dissimilar devices without unnecessary complexity on the processing/receive side of the system. In one embodiment, an entire waveform can be encoded in an XML packet. The XML sequence can grow in size and be split over a plurality of TCP/IP packets when the maximum payload size of TCP/IP packets is reached.

TCP/IP and XML are used at two different network layers. XML is a packet carrying the data. The TCP/IP layer serves as the lines over which the packets travel. TCP/IP functions to provide both acknowledgments and sequence numbers to provide for guaranteed delivery.

FIG. 2 shows a screen view of a display of various patient data with supplemental information of interest. In addition, in this screenshot, an alarm 80 is shown as triggered. In the example, this patient's oxygen level is below a set limit. As a result, a call is placed so that a clinician can check on the patient or medical device associated with the alarm.

In FIG. 3, specific details and various parameters are shown for setting smart alarms for each of the various patients being monitored by the system and methods described herein.

In this display, high and low limits for the various patient parameters can be set by the clinician. In addition, the number of consecutive alarms that can occur within a given time period can be set as an additional safety feature. Finally, the screen also indicates the normal range for a given parameter. In FIG. 4 the user of the system can view all the smart alarms which have been set for every patient. In this display, each smart alarm is listed separately, along with the time of setting, its value, its limits, and any context messages. A nurse call indicator indicates that a smart alarm has occurred and lists the patient and room number.

The user interface 42 is used by the clinician or other user to enter data and retrieve information from the system. FIG. 5 is a screenshot of a graphic user interface suitable for performing various administrative functions relative to the medical device monitoring system described herein. In one embodiment, the screenshot in FIG. 5 is associated with the web interface 58 or the user interface 42 shown in FIG. 1. As shown, the interface includes various mouse-clickable elements that allow a user to perform certain tasks. These tasks include, but are not limited to admitting a new patient, adding new medical devices to the overall monitoring system, decommissioning a medical device (D/C), swapping medical devices between patients, editing patient data, transferring patients, assigning pagers to the patient monitoring staff, updating and setting smart alarms, and adjusting the overall view of the various interface screens. As is generally used in some of the interface embodiments, a bed or room identifier is shown linked to a patient and a device. In addition, one or more of the alerts are also shown. In one embodiment, the term "alert" and "alarm" are used interchangeably and encompass the broadest possible reasonable meaning of either term. In another embodiment, alarms are discrete violations of a particular threshold for a given patient or other medical parameter of interest. For example, an alarm violation may be a high heart rate. In one embodiment, an alert is often contextual. Alarms are often driven by the collected data. In one embodiment, the alerts are the results displayed in response to the triggering of an alarm based on underlying problems detected based on the processing of incoming patient data. For example, an alert may be something displayed to a system user, such as the occurrence of ventricular tachycardia. An electrode falling off a patient is another example of a cause of an alert.

Figure 6:
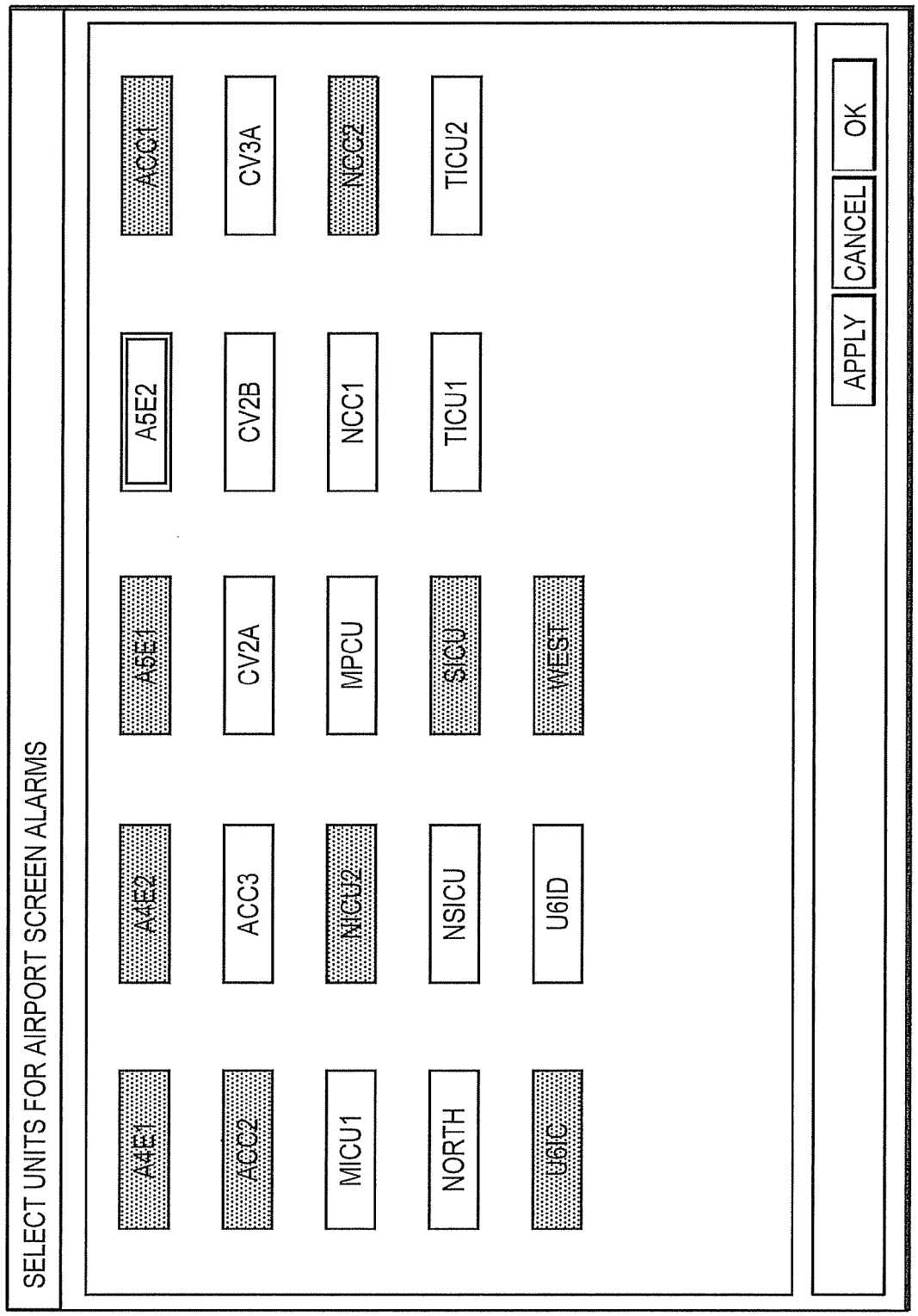
FIG. 6 is a screen shot for a screen for monitoring multiple beds at one time.

FIG. 6 shows an overview screen which allows a user responsible for overseeing multiple beds to see all of them or subset of them simultaneously. As shown in FIG. 6, the individual bed icons are clickable and can be selected to generate expanded display views or to set certain parameters such as screen alarms.

Figure 7:
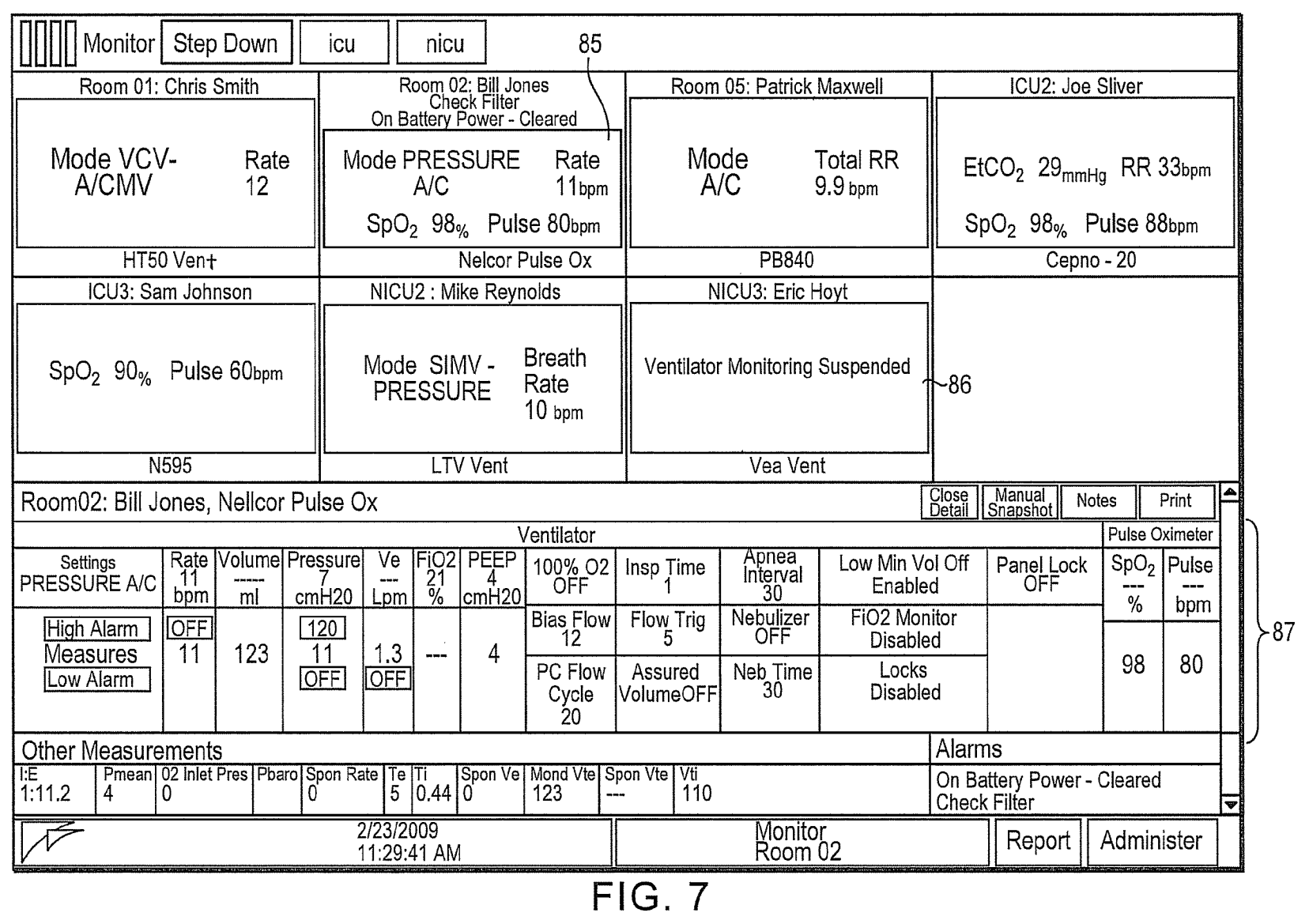

FIG. 7 is another monitor screen useful in monitoring several patients at once. The patient display in the bottom right portion of the screenshot 85 indicates a suspended medical device. A suspended medical device is a device that it is off and not sending data or is a device in a failure state. Because a device standby mode has a "heartbeat indicator" that can be identified across a network link, a standby mode is not typically the same as a suspended mode, although it can be in some device embodiments. In addition, the other six active patient monitoring windows are displaying real time or substantially real time patient data such as pulse rate or blood oxygen levels. Each of these six windows is selectable by a clinician or other user monitoring the patients using a mouse. Clicking on one of the windows 86 causes a drop-down view with additional details 87 to be displayed as shown in FIG. 7.

FIG. 8 depicts a log screen that includes various information of interest as different network, patient, and medical device events occur over time. By recording these events over time, data is preserved in the event of a system failure or if a medical emergency occurs relative to one of the monitored patients.

Figure 9:
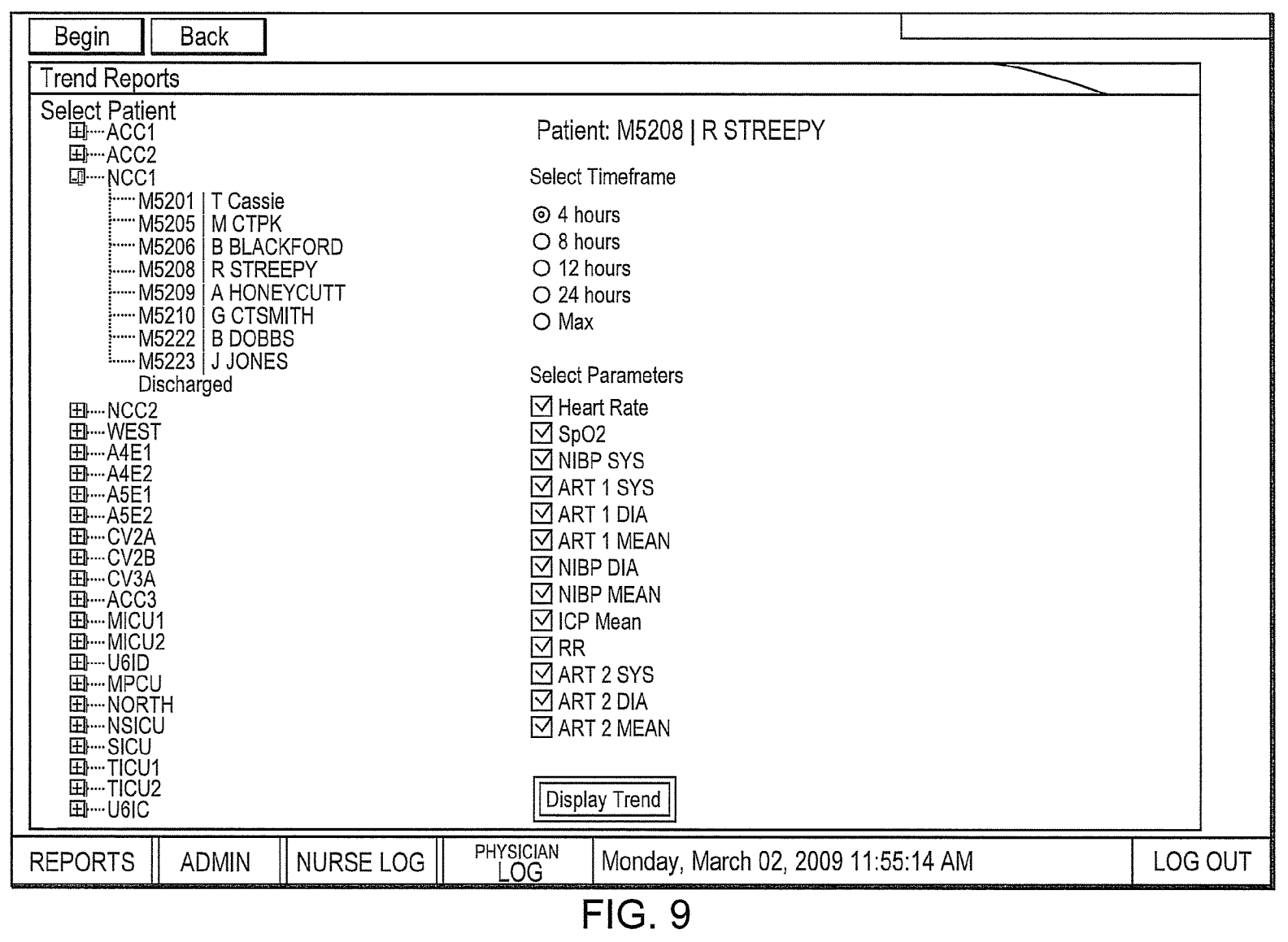

FIG. 9 is a user interface for showing various patient trends over time. By selecting various patients and parameters of interest, plots can be generated to show trends or patterns based on the network-relayed medical device data. In one embodiment, it is possible to show a prioritized list of parameters, alerts, etc. or update the design of the screen based on the device type providing data to the monitoring system. In one embodiment, by prioritizing the list of parameters over time, the most important measurement is at the top of the monitoring screen, but may change over time. For example, if there is no incident associated with a first critical measurement, the next measurement slides up on the screen to the top position in one user interface embodiment. This helps manage screen real estate and keep the user responsible for patient monitoring focused on priority information.

Work flow and patient condition or types of devices attached to a patient can be displayed in one embodiment. For example, workflow can change based on facility type. A ventilator facility in contrast to a cardiology ward may require different alarms or different combinations of alarms. All respiratory parameters are displayed first in a respiratory focused ward. Conversely, cardiac parameters may be displayed first in a cardiac ward.

In one embodiment, a hierarchy for displaying data is used. Based on the condition of the patient, health, diagnosis, ward type, location, etc., information can all be used to adjust the onscreen display of patient or medical device parameters. In one embodiment, the system can program itself with respect to how information is displayed based on historic information or the extent to which certain patient parameters undergo the greatest rate of change. Thus, if blood pressure values collected from a given patient using a medical device keep dropping, the system can change how blood pressure is displayed as part of a user interface. For example, in a list of items on the screen the system can promote blood pressure higher on the list and thus emphasize it as the most important screen element as an indicia of a problem developing with the patient. If something is consistently going wrong with the patient or a parameter value is consistently violating a threshold, using a smart system to draw attention to more frequently occurring threshold violations offer several advantages. In one embodiment, the systems described herein can be used to populate the information systems and databases of hospitals as well as use information from such systems to populate the databases used by the system itself.

Figure 10A:
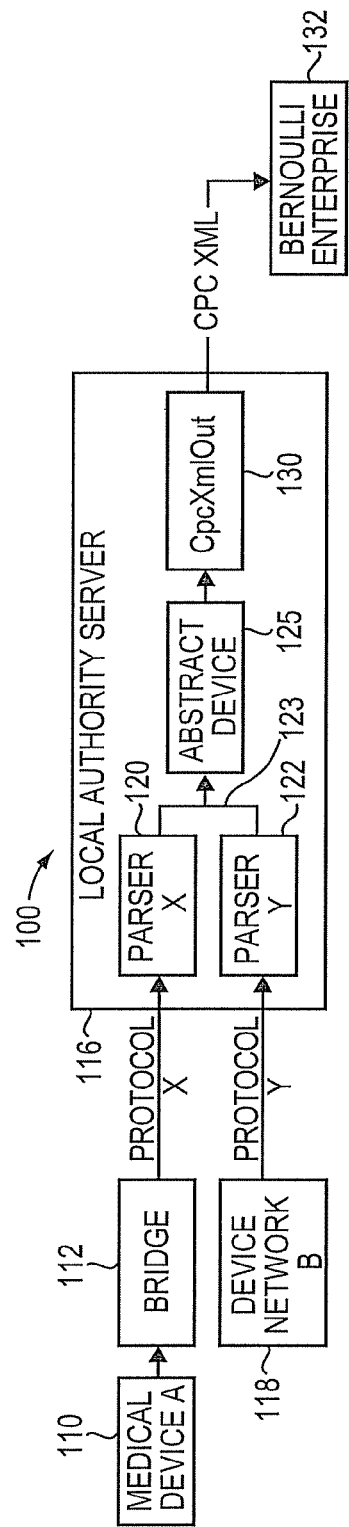
FIG. 10A depicts a system with additional details relating to a local authority server according to an embodiment of the invention.
Figure 10B:
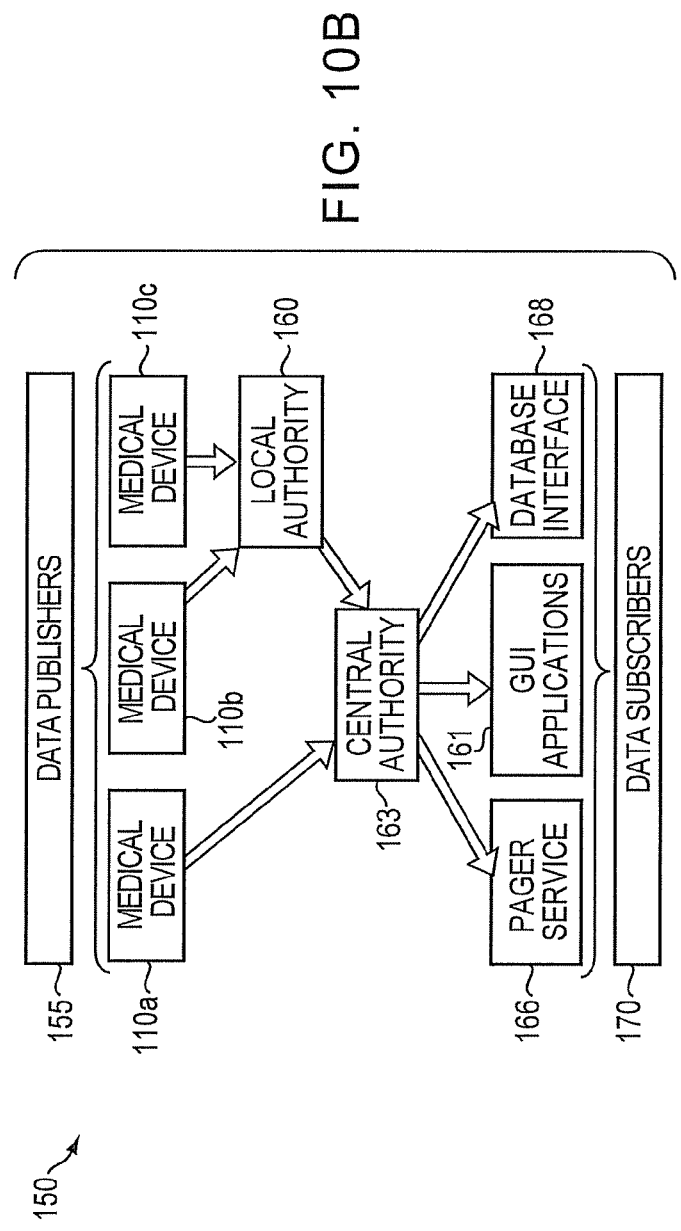
FIG. 10B depicts a system with additional details relating to a local authority server according to an embodiment of the invention and FIG. 11 depicts a block diagram of another system embodiment of the invention.

FIG. 10A shows a medical device data exchange system 100 in which a medical device A, 110 exchanges data with a bridge 112 using a native device language. In turn, the bridge 112 exchanges data with a local authority server 116 using a first protocol, protocol X. In another embodiment, a device network B, 118 also communicates with the local authority server 116 using a second protocol, protocol Y. This device network B may include a network having a plurality of medical devices such as a plurality of beds with a medical device associated with each patient in each of such beds. The local authority server 116 in this embodiment includes a plurality of parsers, such as parser X, 120 and parser Y, 122 as shown, configured to receive different protocols such as protocol X and protocol Y, respectively.

In one embodiment, each respective parser converts the relevant native device or network protocol into a common homogenous system protocol 123 The underlying data received from the medical device 110 or network 118 is communicated to an abstract device 125 using the homogenous protocol. The role of the abstract device 125 is to represent the data packets as they are received in memory. Packet data is sent from the abstract device 125 to a homogenous protocol output 130 (shown as an CPC/XML Output in this example). Once the medical device data has been transformed it is sent to a data monitoring or processing server 132, such as for example a Bernoulli enterprise server. In one embodiment, the medical device data is relayed in an XML format such as CPC/XML.

FIG. 10B shows an overall system or platform 150 in which medical device data is generated as patients are monitored. In one embodiment, the entity that captures the patient data and relays it to the rest of the system is termed a data publisher. The underlying patient data is captured by the medical devices 110A, 110B, and 110C (generally 110). While three medical devices are shown in FIG. 10B for exemplification, it will be appreciated that the system can include any number of medical devices. As discussed above, any component or device (medical device, server, bridge, etc.) that generates and transmits XML is treated by the system as a publisher. Since both TCP/IP sockets are used in combination with XML pages, a two protocol system is used to manage data routed to the overall monitoring system. In one embodiment, medical devices 110a-110c can operate as publishers 155 when they transmit information to one or more authorities. In one embodiment, the medical devices 110 relay data a local authority 160 and/or a central authority 163 as discussed above.

With continued reference to FIG. 10B, in some embodiments, authorities (e.g., local authorities 160 and central authorities 163) can function as subscribers by receiving data from medical devices and as publishers by transmitting data to other system components. While one local authority and one central authority are shown in FIG. 10B for exemplification, it will be appreciated that the system can include any number of such authorities. In one embodiment, local authority 160 functions as a publisher when it relays information to central authority 163. In one embodiment, publishers distribute information to interested data subscribers 170. In one embodiment, this distribution hub which sends processed medical device data to subscribers 170 is a central authority 163. Non-limiting examples of devices and interfaces which can function as subscribers 170 include a pager service 166, GUI applications 161, and database interfaces 168.

Figure 11:
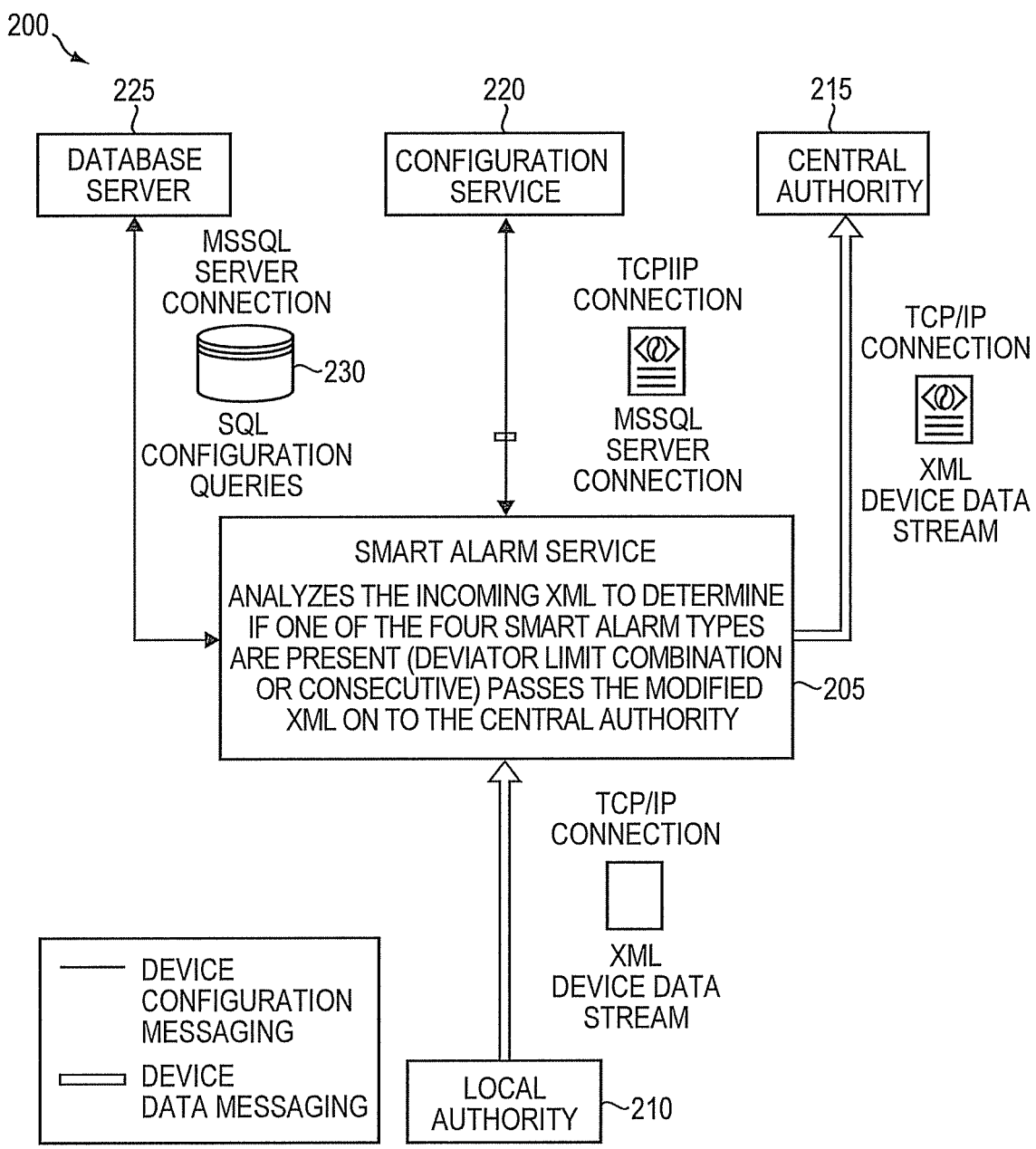

FIG. 11 shows an overall system or platform 200 in which medical device data is generated as patients are monitored with additional details relating to the smart alarm system and example connections and data feeds. As shown, a smart alarm system or service 34 receives (or sends) medical device data in the form of messages or other data elements. The smart alarm system analyzes incoming medical device data encoded in a first protocol, such as XML, to determine if one of several smart alarm types (deviation, limit, combination, or consecutive). Specifically, a deviation alarm is one that is triggered by the deviation of a patient value from a set value. A limit alarm is one that is triggered by a patient value moving outside a specified range. A combination alarm is one in which the occurrence of two or more other alarms causes an alarm. For example, if blood pressure drops outside the normal range and heart rate exceeds the normal range, the alarm will trigger. A consecutive alarm is one that is triggered if a given alarm is triggered more than a set number of times—for example, if at least 2 oxygen desaturations of 30 second duration occur within 2 minutes. Based on the type of alarm found, certain alarm data is passed to the central authority 30. In addition, other data can be passed from the smart alarm system 34 to a configuration service 38 or a database server. In turn, queries 230 or data feeds can originate from the database 50 or the smart alarm system 34 such that the flow of data is bidirectional. The flow of data between the configuration service 38, which indicates when an alarm limit is changed by a user, and the smart alarm system 34 is also bi-directional.

In one embodiment, the system includes a root node containing one or more devices. Typically, an XML document has an inverted tree structure. With respect to XML, a root node indicates the top level of a given document (or the top of the tree directory) from which other child nodes depend. Accordingly, in one embodiment, root node information marks the beginning and end of each message generated on the system. A non-limiting example of root node information is:

<? xml version="1.0" encoding="utf-8"?>

After the root node, specific information relating to a particular medical device or Element cpc is provided:

<! ELEMENT cpc (ipaddress?, device+)>

Continuing down the XML document, specific information relating to the attributes of particular medical device are provided:

```
<! ATTLIST cpc
    type        CDATA #REQUIRED
    bid         CDATA #REQUIRED
    conntype    CDATA #REQUIRED
    datetime    CDATA #REQUIRED
>
```

As shown above, the attribute information (ATTLIST cpc) can include a description (type) of the device element (e.g., a medical device) that generated the message, an identifier (bid) which identifies the message publisher to the system, the connection type (e.g., publisher) and the date and time of the message. The message contains further information about the device element that generated the message.

A non-limiting example of device element information is:

```
<! ELEMENT ipaddress (#PCDATA) >
<! ELEMENT device (status, location?, measurements,
                   settings, alarms, events?)
>
<! ATTLIST device
    bid         CDATA #REQUIRED
    type        CDATA #REQUIRED
    make        CDATA #IMPLIED
    model       CDATA #IMPLIED
    version     CDATA #IMPLIED
>
```

Information such as an identifier (bid) which identifies the message publisher to the system, the type of device element (type) which generated the message, as well as make, model and version of the device element, can be included. Various information regarding the status, location, alarms, events, measurements, etc. of the device element can also be included in the message.

Accordingly, in one embodiment, an exemplary message reads:

Root Node:

```
<? xml version="1.0" encoding="utf-8"?> datetime="2005-05-
24T01:19:19.000Z" bid="LA-10.44.22.1" conntype="publisher"
type="LA">
<device bid="CB19" type="Pulse Oximeter" make="ABC
Corp." model="123" version="" timeout="5000">
```

Location Node:

In this non-limiting example, the location of the device can also be captured by GPS or entered.
<location />

Settings Node:

In this non-limiting example, the following are device settings.
```
<settings>
<s name="BPMprlo">40</s>
<s name="MODE">0</s>
<s name="SPO2prhi">100</s>
<s name="AlarmSilence">OFF</s>
<s name="AlarmOff">OFF</s>
<s name="Protocol">ABCnet</s>
</settings>
```

Measurements Node:

In this non-limiting example, the following are values the device is measuring.
```
<measurements>
<m name="SPO2">75</m>
<m name="BPM">60</m>
<m name="PA">5</m>
```

Waveform Node:

In this non-limiting example, MG is the measurement group. RT_Data is the name of a waveform such a cardiac or lung function waveform based on data obtained from the medical device of interest.
In some embodiments, binary data cannot be used, so waveform data is encoded below by a sequence of characters. In this example, the waveform is encoded by the sequence "HR4fIys.."
```
<mg name="RT_DATA">
<m name="Wave">HR4fIys/SU1LSEVCQD48Ojg2NDMyMTAvLisdDQEBAwUICw4QEhUWGBkaGxw
dHh8lMEJLTUtIREE/PTs5NzY0MzIxMC8uKRsKAQACBgkMDhATFB
YXGRobHR0fICU0Q0xNSkZEQTw6OTc1NDMyMDAvLiUYBgAABAcJDA8RExUXGBkbHB0eIi4/S
UxKR0VCPz07OTc2NTMyMTAvLSocDQIAAwYICw4RExQWFxgaGx0eHh8lMUVLTEtHREE/PTo5
NzU0MzIxMC8tKhg=</m>
<m name="PointsBytes">1</m>
<m name="Min">0</m>
<m name="Points">200</m>
<m name="Max">255</m>
```
In this non-limiting example, the scale of the waveform is 255 units.
```
<m name="Offset">57.000000</m>
<m name="Gain">1.000000</m><m name="Hz">81.379997</m>
```
In this non-limiting example, every second of data is represented by 81.379997 points on the scale.
```
</mg>
</measurements>
```

Alarm Node:

```
<alarms>
<a name="NODATA">ALARM</a>
In this non-limiting example, if the medical device stops sending data,
an alarm is triggered.
</alarms>
</device>
</cpc>
```

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

What is claimed is:

1. A processor-based system for providing for the display of data from a plurality of heterogeneous medical devices, the system comprising:
   a smart alarm subsystem for determining whether the data from one or more medical devices of the plurality of heterogeneous medical devices meets predetermined criteria for triggering at least one each one of a limit alarm, a deviation alarm, a consecutive alarm, and a combination alarm;
   a central authority subsystem in communication with the smart alarm subsystem;
   a user interface in communication with the central authority subsystem; and
   a database subsystem in communication with the central authority subsystem;
   wherein the central authority subsystem transmits the data from the plurality of heterogeneous medical devices for display by the user interface and for storage by the database subsystem, substantially simultaneously,
   wherein the user interface sets parameters in the smart alarm subsystem and receives alarms from the smart alarm subsystem through the central authority subsystem, and
   wherein the alarm is triggered by at least each one of: a parameter for a data value from one medical device as, a limit alarm; deviates from a setting by a clinician as a deviation alarm; a combination of parameters occurs for data values from more than one medical device, as a combination alarm; and as a result of an alarm being triggered more than a predetermined number of times, as a consecutive alarm.

2. The processor-based system for providing for the display of data from a plurality of heterogeneous medical devices of claim 1 further comprising a local authority subsystem in communication between the plurality of medical devices and smart alarm subsystem and in communication between the plurality of medical devices and the central authority subsystem.

3. The processor-based system for providing for the display of data from a plurality of heterogeneous medical devices of claim 2 wherein the local authority transforms the data from the plurality of heterogeneous medical devices from a first protocol to a second protocol.

4. The processor-based system for providing for the display of data from a plurality of heterogeneous medical devices of claim 3 wherein the first protocol is a native device protocol and the second protocol is a homogeneous system protocol.

5. The processor-based system for providing for the display of data from a plurality of heterogeneous medical devices of claim 3 wherein the homogeneous system protocol is XML.

6. The processor-based system for providing for the display of data from a plurality of heterogeneous medical devices of claim 2 further comprising a demultiplexer in electrical communication with both the local authority subsystem and the plurality of heterogeneous medical devices.

7. The processor-based system for providing for the display of data from a plurality of heterogeneous medical devices of claim 2 wherein the local authority publishes the data to either the smart alarm subsystem or the central authority subsystem.

8. The processor-based system for providing for the display of data from a plurality of heterogeneous medical devices of claim 1 wherein the smart alarm module is also in electrical communication with the database subsystem.

9. The processor-based system for providing for the display of data from a plurality of heterogeneous medical devices of claim 1 further comprising a database interface in electrical communication with the central authority subsystem and the database subsystem.

10. The processor-based system for providing for the display of data from a plurality of heterogeneous medical devices of claim 1 further comprising a network server in electrical communication with both the database subsystem and a web interface.

11. A method for providing for the display of data from a plurality of heterogeneous medical devices, the method comprising the steps of:
    receiving data from the medical devices by a central authority subsystem through a smart alarm subsystem;
    setting parameters in the smart alarm subsystem and receiving alarms from the smart alarm subsystem through the central authority subsystem;
    substantially simultaneously transmitting the data by the central authority subsystem to both a user interface and a database; and
    displaying the data by the user interface,
    wherein an alarm is triggered by at least each one of: a parameter for a data value from one medical device as, a limit alarm, deviates from a setting by a clinician as a deviation alarm; a combination of parameters occurs for data values from more than one medical device, as a combination alarm; and, as a result of an alarm being triggered more than a predetermined number of times, as a consecutive alarm.

12. A processor-based system for providing for the display of data from a plurality of heterogeneous medical devices, the system comprising:
    a smart alarm subsystem for determining whether the data from one or more medical devices of the plurality of heterogeneous medical devices meets predetermined criteria for triggering an alarm;
    a central authority subsystem in communication with the plurality of heterogeneous medical devices; and
    a user interface in communication with the central authority subsystem; and
    a database subsystem in communication with the central authority subsystem,
    wherein the central authority subsystem transmits data from the plurality of heterogeneous medical devices substantially simultaneously to the user interface for display and to the database subsystem for storage,
    wherein the user interface sets parameters in the smart alarm subsystem and receives alarms from the smart alarm subsystem through the central authority subsystem,
    wherein a medical device transmits data directly to the smart alarm subsystem, and wherein the alarm is triggered by at least each one of: a parameter for a data value from one medical device as, a limit alarm; deviates from a setting by a clinician as a deviation alarm; and a combination of parameters occurs for data values from more than one medical device, as a combination alarm; and as a result of an alarm being triggered more than a predetermined number of times, as a consecutive alarm.

13. The processor based system of claim 12 wherein the smart alarm is set in response to the rate of change of a parameter.

* * * * *